US010524757B2

(12) United States Patent
Julien et al.

(10) Patent No.: US 10,524,757 B2
(45) Date of Patent: Jan. 7, 2020

(54) METHOD AND SYSTEM FOR TAKING MEDICAL RADIOLOGY IMAGES WITH CONTROL OF THE STOPPING OF THE X-RAY SOURCE

(71) Applicant: E2V SEMICONDUCTORS, Saint Egreve (FR)

(72) Inventors: Florian Julien, Voiron (FR); Laurent Lussereau, Méaudre (FR); Pascal Pellet, Grenoble (FR); Yves Delzoppo, Saint-Égrève (FR)

(73) Assignee: TELEDYNE E2V SEMICONDUCTORS SAS, Saint-Égrève (FR)

( * ) Notice: Subject to any disclaimer, the term of this patent is extended or adjusted under 35 U.S.C. 154(b) by 242 days.

(21) Appl. No.: 15/507,864

(22) PCT Filed: Aug. 11, 2015

(86) PCT No.: PCT/EP2015/068492
§ 371 (c)(1),
(2) Date: Mar. 1, 2017

(87) PCT Pub. No.: WO2016/034379
PCT Pub. Date: Mar. 10, 2016

(65) Prior Publication Data
US 2017/0281115 A1    Oct. 5, 2017

(30) Foreign Application Priority Data
Sep. 2, 2014   (FR) ..................... 14 58200

(51) Int. Cl.
*A61B 6/14*    (2006.01)
*G01N 23/04*   (2018.01)
*A61B 6/00*    (2006.01)

(52) U.S. Cl.
CPC .............. *A61B 6/542* (2013.01); *A61B 6/145* (2013.01); *A61B 6/4233* (2013.01); *A61B 6/461* (2013.01); *A61B 6/548* (2013.01); *A61B 6/563* (2013.01)

(58) Field of Classification Search
CPC ....... A61B 6/06; A61B 6/4071; A61B 6/4078; A61B 6/4241; A61B 6/4258;
(Continued)

(56) References Cited

U.S. PATENT DOCUMENTS 5,844,961 A * 12/1998 McEvoy .................. H05G 1/64
378/98.8
6,404,854 B1   6/2002 Carroll et al.
(Continued)

FOREIGN PATENT DOCUMENTS

| EP | 1146559 A1 | 10/2001 |
| EP | 1857049 A1 | 11/2007 |
| EP | 2180343 A2 | 4/2010 |

OTHER PUBLICATIONS

International Search Report and Written Opinion for PCT/EP2015/068492, dated Oct. 23, 2015.

*Primary Examiner* — Irakli Kiknadze
(74) *Attorney, Agent, or Firm* — Pilloff & Passino LLP; Sean A. Passino; Rachel K. Pilloff

(57) ABSTRACT

A medical radiology system comprises an external x-ray source (1) and a CMOS image sensor (2) that is connected via a USB link (4) by way of USB peripheral of a device (3) for digitally processing the image data of the sensor. A tracking device is placed on the USB link (4) in order to continuously read and decode the data transmitted over this link in a way that is transparent to the device and to the sensor, and to detect, in the transmitted data stream, one particular datum (XAMC=1) representing a signal indicating detection, by the sensor, that a sufficient dose of radiation
(Continued)

has been received. On detection of this particular datum, the tracking device sends an electrical signal Stop-X to the radiation source, in order to stop the emission of the radiation. The system is especially suitable for taking dental radiology images with an intra-oral CMOS sensor.

18 Claims, 5 Drawing Sheets

(58) Field of Classification Search
CPC ... A61B 6/4291; A61B 6/4429; A61B 6/4441; A61B 6/4476; A61B 6/482; A61B 6/485; A61B 6/505; A61B 6/5217; A61B 6/5282; A61B 6/542; A61B 6/145; A61B 6/4233; A61B 6/461; A61B 6/548; A61B 6/563; A61B 6/14; A61B 6/508; A61B 2562/187; A61B 6/425; A61B 6/4488; A61B 6/56; A61B 2562/02; A61B 2562/0233; A61B 2562/046; A61B 6/5205; A61B 2090/0436; A61B 2090/0481; A61B 2562/164; A61B 5/0088; A61B 5/682; A61B 6/107; A61B 6/4035; A61B 6/4208; G01N 2223/076; G01N 2223/0763; G01N 2223/1013; G01N 2223/1016; G01N 23/087; H01J 35/00; H01L 2924/0002; H01L 27/14618; H01L 2924/00; H01L 27/14601; H01L 27/14623; H01L 27/14658; H01L 27/14806; H01L 27/14818; G01T 1/2018
USPC ............... 378/38, 62, 97, 98.8, 168, 191
See application file for complete search history.

(56) References Cited

U.S. PATENT DOCUMENTS

| | | | |
|---|---|---|---|
| 8,119,990 B2* | 2/2012 | Zeller | ............ G01T 1/17 250/370.09 |
| 2005/0253944 A1 | 11/2005 | Olsen et al. | |
| 2013/0077744 A1 | 3/2013 | Kamiya | |
| 2013/0223592 A1 | 8/2013 | Sato | |
| 2015/0250436 A1* | 9/2015 | Hyde | ............ A61B 6/145 378/62 |

* cited by examiner

METHOD AND SYSTEM FOR TAKING MEDICAL RADIOLOGY IMAGES WITH CONTROL OF THE STOPPING OF THE X-RAY SOURCE

FIELD

The invention relates to a method and system for taking medical, and in particular dental, radiological images allowing the exposure time of a patient to x-rays to be minimized while ensuring images of good quality are captured.

PRIOR ART

A medical radiology system comprises as schematically illustrated in FIG. 1, an x-ray source 1, an image sensor 2 that is sensitive to the x-ray radiation and a device 3 for processing and displaying the images delivered by the sensor.

In the illustrated example, it is a question of a dental radiology system. The image sensor is placed inside the mouth of the patient, behind the object, i.e. tooth, to be imaged. Intra-oral sensors are spoken of. The x-ray source is equipped with an orientable head 10 in order to emit radiation toward the cheek of the patient, in the direction of the sensor. The x-ray dose is parameterized beforehand by the practitioner by means of a control pad such as a remote control 11. The sensor transmits the collected image data to the processing and displaying device 3, which is generally in this case a (desktop, laptop, etc.) computer of the practitioner. In the invention, systems in which the sensor and the computer communicate via a wired USB link 4 are more particularly of interest.

It is known that the market share of CMOS image sensors has substantially increased, replacing CCD sensors in many fields. This is also the case in the field with which we are concerned. Thus, the latest dental radiology systems use, as intra-oral sensor, a CMOS sensor that is connected to the computer by a wired link 4 complying with the USB (universal serial bus) protocol. Patent EP 1,146,559 describes an example thereof. The use of a USB interface is very advantageous. The sensor becomes a simple "USB peripheral" in the same way as a printer, scanner, etc. It may be easily connected/disconnected from any computer of the dentist's surgery having the right control software. Since the power consumption of an intra-oral CMOS sensor is low, it is also powered via the USB link by the computer. Thus specific power-supply modules (batteries) are avoided.

TECHNICAL PROBLEM

A problem that arises again and again with dental radiology systems, and more generally the medical radiology systems, is that of the duration of the x-ray irradiation. This duration must be sufficient to be able to obtain a high-quality image, i.e. one that is neither underexposed nor overexposed. At the same time, the duration of exposure of the patient, and also of the practitioner, to the x-ray radiation must be as short as possible.

To address this problem, x-ray sources have been improved to optimize the characteristics of the radiation and to decrease the required dose. Improvements have also been made in order to facilitate the parameterization thereof by the practitioner depending on the zone of interest (which tooth) and the weight of the patient. For each image captured, a corresponding dose is defined (voltage (kV), current (mA), exposure time (ms)) by parameters set by the practitioner depending on the patient (age) and the tooth in question. Nonetheless, this parameterization remains imperfect as it depends on the experience of the practitioner, but also because the type of tooth and the age of the patient is not really enough information to perfectly parameterize the dose to be used. Thus, there is a high risk that an under or overexposed image will be obtained.

Another difficulty is related to the way in which the various elements of the system interoperate. Specifically, the sensor and the source are devices that operate independently of each other; there is no direct channel of communication therebetween. Thus, once parameterized, when the dentist then triggers the source (via the remote control 11—FIG. 1) it omits the defined x-ray dose for the set exposure time. However, the sensor is not provided with this exposure start (or end) information directly.

However, to obtain an image of best possible quality, with the least possible noise, the integration phase of the sensor must begin when the sensor actually receives the radiation. Before, the sensor senses only noise, in particular the dark noise of the photosensitive elements of the pixels.

Thus, in these radiographical image capturing systems, the sensors conventionally comprise means for detecting x-ray radiation. As soon as radiation is detected, by specific integrated means, it triggers the integration phase.

Various detecting techniques are used in practice. Thereamong, mention may be made of that schematically illustrated in FIG. 2, which consists in providing on the periphery of the matrix 20 of pixels of the sensor 2, an array 21 of detecting photodiodes that are coupled to means 22 for reading out and comparing to a preset threshold REF. In this case, provision is generally made for 2 columns of photodiodes in series, one on each side of the matrix of photosensitive pixels. The current delivered by these photodiodes is compared to the preset threshold REF. In the absence of radiation, the signal essentially corresponds to noise, mainly dark current. In the presence of x-ray radiation, the signal level substantially increases. As soon as the threshold REF is exceeded, a signal Start-X indicating the start of the radiation is activated. The command/control unit of the sensor (not shown) which delivers the various signals sequencing the integration and read-out phases of the pixels, receives this signal Start-X and launches the integration phase of the sensor.

This integration phase has a duration TINT that is preprogrammed to a chosen value, for example 200 ms, that is equal or slightly longer than the maximum possible exposure duration of the employed x-ray source. Typically, the activation of the signal Start-X signaling the start of the exposure to radiation triggers a counter programmed to count down the duration TINT. At the end of the countdown, the integration period terminates and the phase of read-out of the sensor and transfer of the image data is triggered.

In certain sensors, provision is also made to detect the end of the x-ray radiation, based on the fact that when the radiation is about to stop the signal level ceases to vary. For example, the same set of photodiodes shown in FIG. 2 may be used, the detection consisting in monitoring whether the signal level is still changing or not. In this way, it is possible to send a signal End-X indicating the end of the emission of the x-ray radiation. This signal allows the integration phase to be terminated and the read-out to be engaged, without waiting for the end of the duration TINT. Other techniques for detecting the end of the emission of radiation may be used. For example, patent U.S. Pat. No. 6,404,854B describes a method for nondestructively reading the pixels of the matrix, making it possible to detect that the signal level of certain pixels of the matrix is no longer changing, indicating that the source has ceased to emit.

These detections by the sensor thus allow information on the time of exposure to the radiation emitted by the source to be collected and the start of the integration and even the end of the integration of the sensor to be synchronized with the actual exposure time of the radiation source, limiting the amount of noise in the data delivered by the sensor. FIG. 3 shows a timing diagram with an x-ray emission time (Tdose, for example 100 ms), and a sensor integration time (TINT, for example 200 ms) before a read-out of the integrated signal. The integration time is triggered by the start of emission and terminates after the end of the emission.

However, it has been seen that the dose parameterized in the source may not be "optimal" in terms of image quality. In particular, the exposure time Tdose parameterized in the x-ray source may in fact be slightly too long, this then leading to a saturation of the pixels. The image will be overexposed.

Specifically, there is no intermediate state between the zone of linear operation and the zone of saturation of the pixels, as illustrated in FIG. 4. The operating zone of the sensor corresponding to an optimal signal-to-noise ratio is indicated by hatching in this figure: as is well known, it corresponds to a pixel signal level corresponding to about ¾ of the dynamic range of the sensor and, between the point of entry into this zone and that of exit therefrom, only a small amount of time passes, 10 ms for example. In the example, a good signal-to-noise ratio is obtained after 55 ms of exposure at the radiation dose, and from 80 ms the zone of saturation is entered. Thus, with an exposure time to the x-ray radiation that is slightly too long, the image changes, in a short lapse of time, from one of good quality to one exhibiting saturated grey levels and an absence of contrast in the zone or zones of interest. But if the image is saturated, it will not be usable. It will therefore be necessary to retake the image, this necessarily requiring re-parameterization of the image capture to decrease the dose, and thus to subject the patient to another dose of radiation. Furthermore, the practitioner loses time making these adjustments and taking these new images.

It will thus be clear that image quality and the need to subject the patient to a minimum dose of radiation are closely related problems. Thus, it is not enough to be able to parameterize the source; and it is not enough for the sensor to be able to detect the start and end of the time of exposure to the dose emitted by the external source. It is also necessary for the sensor to be able to stop this external source dynamically, during the image capture process, and more particularly during the integration phase, when the signal level measured by at least some of the pixels of the sensor corresponds to an optimal level.

In order to prevent pixel saturation, it is known to make provision, in sensors and in particular in CMOS sensors, to control exposure time by repeatedly and nondestructively reading at least certain pixels of the matrix during the integration period. These chosen pixels are read nondestructively, and the signal level obtained is compared to a corresponding set threshold that is defined depending on characteristics of the sensor. When this threshold is reached or exceeded by a certain number of "reference" pixels, it is decided that the exposure to the radiation is sufficient and ensures a good image quality. A corresponding signal is activated.

When the read-out of these pixels is said to be nondestructive, what is meant is that these pixels are not reset after the read-out: they continue to integrate charge. Thus, the information contained in these pixels is not lost. The control unit of the sensor, which sequences the various phases by delivering signals allowing read-out and analogue-conversion circuits of the sensor to be addressed and activated is then configured to allow such a repeated nondestructive read-out to be carried out during the integration phase.

This nondestructive read-out may be carried out with any type of CMOS pixel structure, but its implementation is facilitated in the case of a three-transistor structure (3T pixels), in which it is the signal level obtained directly by the photosensitive element (and not that of an associated storage well) that is read. Thus taking the example of a 3-transistor CMOS sensor (3T pixel) with a correlated-double-sampling (CDS) read-out and digital-analogue conversion, the CDS read-out of the pixels conventionally comprises the following phases: each pixel is initialized at the start of the integration phase, and an initialization level of the pixel is stored in memory. At the end of the integration phase, the photodiode of the pixel contains an amount of charge representative of the illumination received by the photodiode in this phase. The pixel is read to obtain a signal level representative of this illumination. The CDS read-out performs a subtraction between the initialization level and this signal level, to obtain a measurement representative of the illumination but free from a correlated noise component. Depending on the sensors, this subtraction may be performed digitally or analogously. The pixel is then reset for the following integration period.

If the pixel is not reset, the read-out is nondestructive: the pixel will continue to accumulate charge in addition to that already accumulated. It is therefore possible to continuously check the signal level throughout the integration phase, without loss of information.

Patent application US 2005/0253944 implements such a nondestructive read-out in a CMOS sensor, to stop light exposure by activating a shutter or turning off the integrated light source (LEDs) in a context in which the light source is integrated into or connected to the sensor, and in particular in an endoscopic capsule containing a CMOS sensor.

In the invention, it is desired to be able to stop the x-ray source on the basis of such information delivered by the sensor, but in the context described and illustrated in FIG. 1 (of an external radiation source that is independent of the sensor) in which there is no direct link or communication between the sensor and the source of radiation and in which the sensor is connected as a USB peripheral of a host computer.

The technical problem to be addressed in this particular context is that it is not known how to transmit this information to the source with sufficient rapidity or reliability.

Specifically, the USB communication protocol does not make provision for a mode for rapidly communicating a particular event, that allows the USB periphery to avert, i.e. immediately interrupt, the host computer.

The USB protocol indeed provides what is called a transfer "interrupt" mode, but it is not a question of an interrupt in the common sense of the word, i.e. such that the computer stops any current processing to give priority treatment to the interrupt.

This transfer interrupt mode of the USB protocol only allows transmission of particular data that are restricted in number and typically events, such as for example the exposure start event Start-X, which event will possibly be used by the computer in the processing of the image data that it will subsequently receive.

In this interrupt transfer mode of the USB protocol, the computer in fact regularly interrogates the peripheral, at what is called a polling frequency that is defined for the peripheral in question, in order to determine whether the peripheral has an "event" to transfer in this mode. In response, the peripheral returns a data frame containing the event or events that it has to transmit. In practice, in the frame, the event is coded in the form of an event number (the event numbers form part of the descriptors of the peripheral and are known to the computer).

With such a communication mode, it is not in practice possible to transfer the information to the source with sufficient rapidity to stop it. In the best case, it is necessary to count at best twenty milliseconds starting from the moment when the event is available (detected) in the sensor, and transferred to the source by the computer. As may be seen in FIG. 4, twenty milliseconds is already too long: the zone of saturation of the one or more pixels will already have been entered. Furthermore, in the worst case, the event may even not be treated, in particular in case of fortuitous malfunction of the computer.

SUMMARY

The idea behind the invention is to install a feedback loop between the sensor and the x-ray source in order to stop the emission of x-rays as soon as a sufficient dose has been received by the sensor, by placing, on the USB link, a tracking device that will detect the corresponding event sent by the sensor in the data stream transmitted over the link, and transmit an electrical signal directly to the source, to stop the radiation. The tracking device carries out the detection in a way that is transparent to the sensor and to the host computer.

More precisely, the invention relates to a method and system for taking images in medical radiology, the system comprising an external x-ray source and a CMOS image sensor that is connected via a USB link by way of USB peripheral of a device for displaying and processing the image data of the sensor. The method comprises reading and continuously decoding the data transmitted over the USB link, in a way that is transparent to the device and to the sensor, in order to detect, in the transmitted data stream, one particular datum (XAMC=1) representing a signal indicating detection, by the sensor, that a sufficient dose of radiation has been received and, on detection of this particular datum, sending an electrical signal to the radiation source in order to stop the emission of the radiation. The method is in particular applicable to dental radiological image capture by an intra-oral CMOS sensor.

Preferably, at least one other electrical signal is sent to the source, to command an indicator light.

The particular datum to be detected and decoded is a datum transmitted by the sensor over the USB link in an interrupt transfer mode.

The system for taking images according to the invention comprises an external x-ray source, a CMOS sensor comprising a matrix of pixels, which sensor is placed facing the source, and a device for digitally processing the images delivered by the sensor, wherein the sensor is connected as a USB peripheral of said processing device, via a serial USB link. It is characterized in that:

the sensor is configured to detect that a sufficient dose of x-rays has been received and to transmit a corresponding particular datum over the USB link;

a tracking device is connected to the USB link, between the sensor and the device, said tracking device furthermore having an electrical connection to the source, in order to transmit at least one electrical signal (Stop-X) to the source in order to command the stoppage of the x-ray source, said tracking device being able to detect said particular datum in the data stream transmitted over the USB link, and to activate said electrical signal (Stop-X) commanding the stoppage of the source.

According to another aspect of the invention, the method preferably comprises:

the definition of N regions of interest in the matrix of pixels of the sensor, N being an integer at least equal to two, where the defined regions of interest are sub-matrices of pixels of equal size, all with the same number of rows and the same number of columns, repeated and nondestructive read-out of the pixels of each of the regions of interest during the duration of the integration phase of the sensor, with, for each of the regions of interest, calculation of an average value of the signal level read from the pixels of the one or more regions of interest and comparison to a preset threshold value, and a detection signal indicating that a sufficient dose of radiation has been received is activated by the sensor and a corresponding piece of information is transmitted over the USB link by the sensor as soon as, for one or more of the N regions of interest, the calculated average value exceeds the threshold value.

The method is advantageously used to take dental radiological images by means of an intra-oral CMOS image sensor.

BRIEF DESCRIPTION OF THE DRAWINGS

Other features and advantages of the invention will become apparent on reading the following detailed description, which makes reference to the appended drawings, in which.

DETAILED DESCRIPTION

FIGS. 5 to 9, which illustrate the invention, use, for common elements, the same references as in FIGS. 1 to 4, which have already been described.

The method for taking radiological images uses an intraoral CMOS image sensor 2 to transmit a data signal XAMC to the device 3 indicating that a sufficient dose of radiation has been received, where the notion of sufficiency is to be understood with respect to an optimal image quality.

Figure 1:
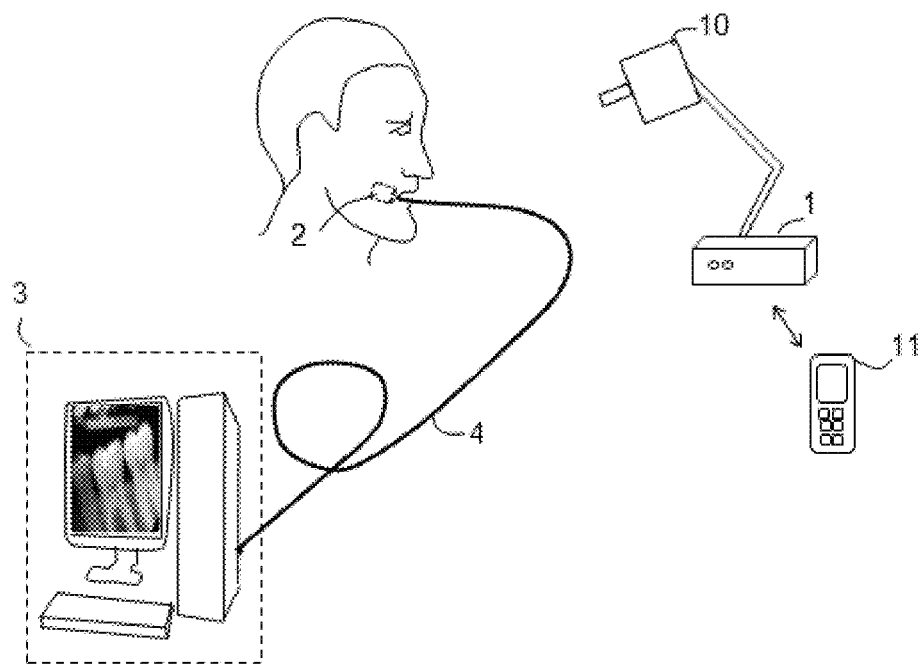
FIG. 1, which was described above, shows a dental radiology system.
Figure 2:
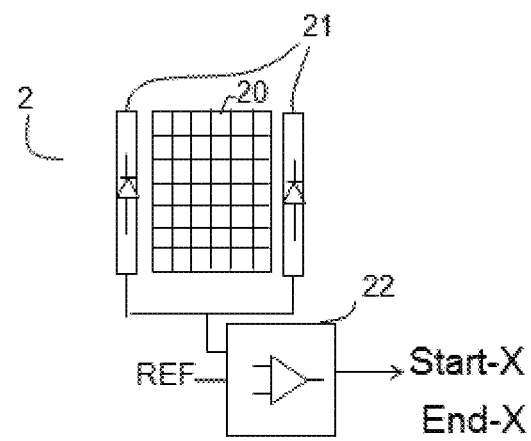
FIG. 2 schematically shows an intra-oral sensor incorporating means for detecting the start of an exposure to x-rays.
Figure 3:
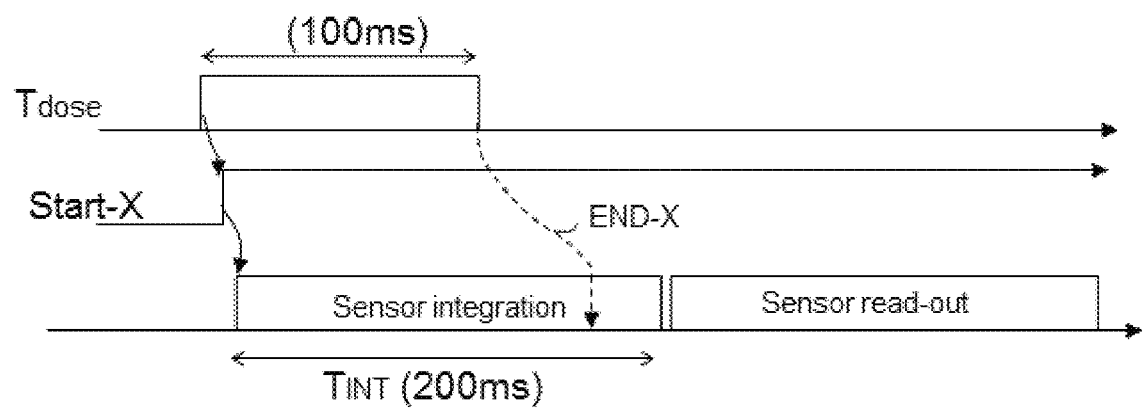
FIG. 3, which was described above, is a signal timing diagram showing, on the one hand, the exposure time parameterized in the source, and, on the other hand, the activation of the integration and read-out phases in the sensor of FIG. 2.
Figure 4:
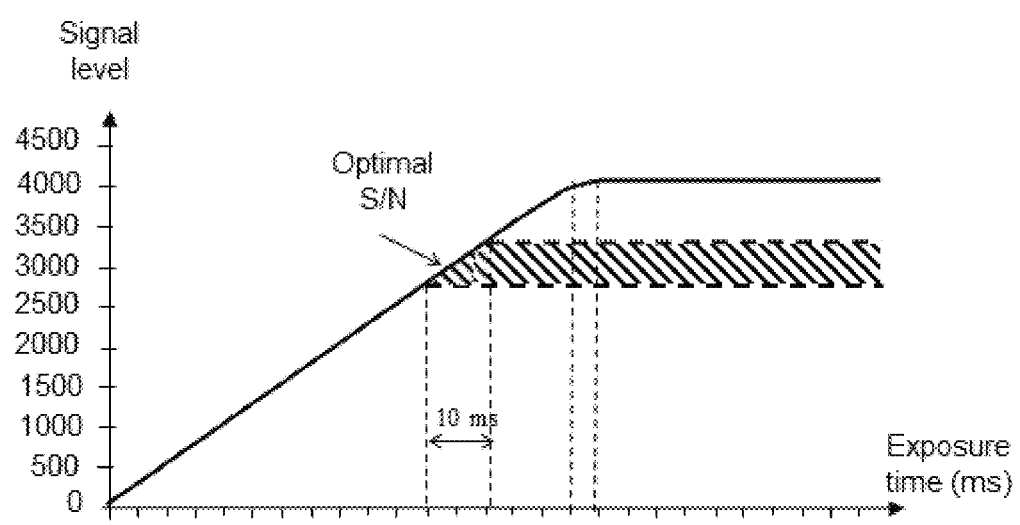
FIG. 4, which was described above, illustrates the sensitivity of the sensor as a function of the duration of exposure to the x-ray radiation.
Figure 5:
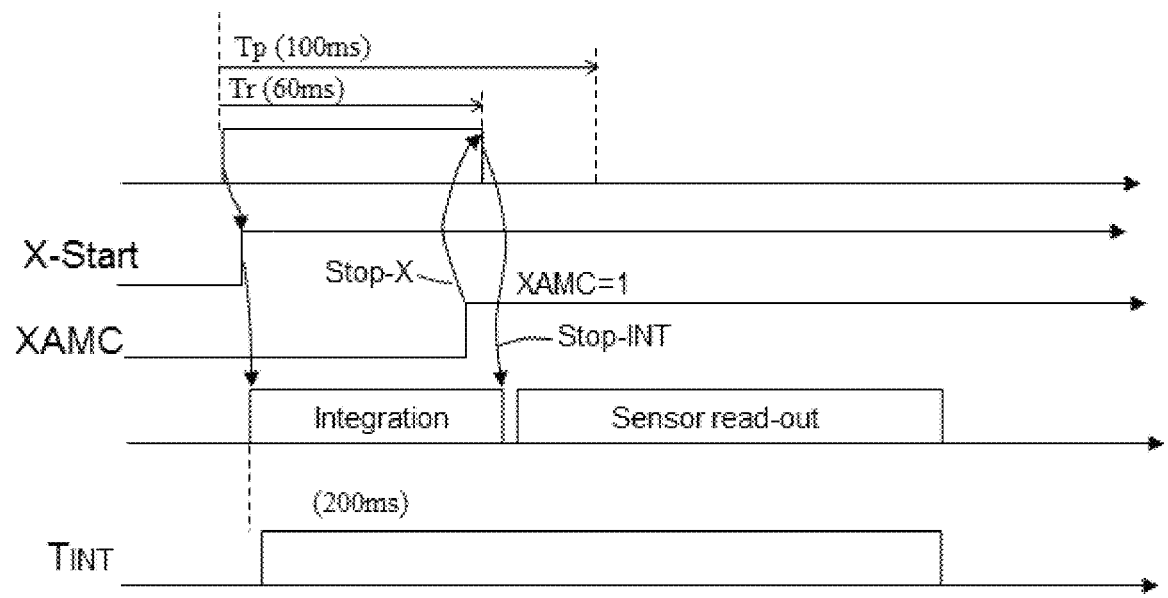
FIG. 5 is a timing diagram of the signals used in the invention to control the duration of exposure of the sensor with a view to guaranteeing an image of optimal quality and a minimum exposure time.

According to the invention, and as illustrated in the timing diagram in FIG. 5, the method for taking images uses this signal XAMC, in a way that will be described in detail below, to immediately stop the x-ray source, by means of a signal Stop-X, without transition via the host device, the response time of which is too slow on account of the durations in question.

The integration time of the sensor subsequently stops when the source ceases to emit x-rays; the sensor itself detects the absence of irradiation when the source is no longer emitting (detection by photodiodes such as 21 for example) and it triggers the stoppage of the integration. The integrated signals may then be read. The integration phase will therefore in general stop (Stop-INT) before the preprogrammed duration TINT. Specifically, it has been seen that this duration TINT is programmed, depending on characteristics of the radiation source, to a value slightly higher than the maximum exposure time of this source. Thus, in the illustrated example (FIG. 5), the source and the integration phase are both stopped after a time Tr, here about 60 ms, after the start of the exposure to x-ray radiation, whereas the dose parameterized in the source provided for an exposure time Tp of 100 ms. Equally, the read-out phase may begin immediately after, without waiting for the end of the countdown of the duration programmed for the integration time TINT (here 200 ms).

Thus, in an image capturing process according to the invention, the integration phase of the sensor may advantageously start with a signal Start-X generated internally by the sensor, and that corresponds to the detection of the start of the reception of x-ray radiation, and terminate with whichever of the following two events occurs first: the interruption of the source following the passage to the active level (1 in the example) of the signal XAMC, indicating that a sufficient dose of radiation has been received, or else the end of the count (countdown) of the programmed maximum duration TINT from the start of the integration phase.

Figure 6:
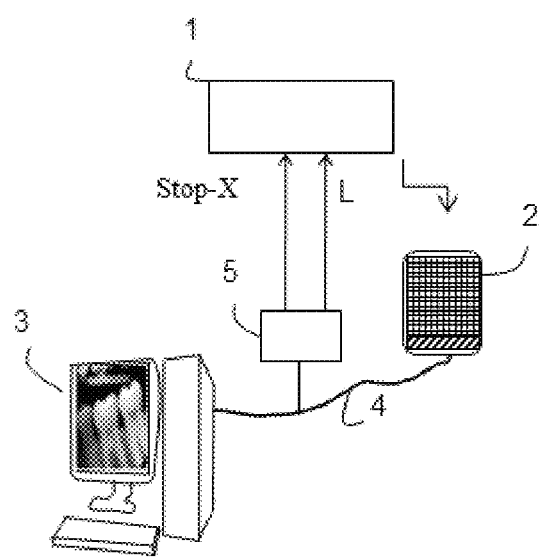
FIG. 6 illustrates a dental radiology system according to the invention, comprising a tracking device placed on the USB link between the sensor and the computer.

This method for taking images allowing image quality to be optimized with a minimum exposure of the patient to radiation is obtained using a tracking device 5 on the USB link 4 between the sensor and the computer, as illustrated in FIG. 6.

It is a question, for this tracking device, of detecting, in a way that is transparent to the sensor and to the host device 2, i.e. without disrupting the communication between these two devices, the transmission by the sensor of information that corresponds to the activation of the signal XAMC.

It will be recalled that when the signal XAMC is activated (XAMC=1 in the example) a corresponding event, that for the sake of simplicity is denoted the XAMC event, is transmitted by the sensor, and more precisely by a USB interface circuit implemented in the sensor, to the host computer 3 over the USB link 4. The XAMC event is transmitted over the USB bus via an endpoint dedicated, in the USB protocol, to the management of events. It possesses a specific code allowing it to be distinguished from other events.

The tracking device 5 thus has the role of detecting the transmission of an XAMC event in the data stream carried by the USB link 4, without disrupting this link, i.e. without interrupting or disrupting the communication between the computer and the sensor. The detection consists in reading all the data transiting the differential pair of the USB link and then decoding them in order to detect therein the data featuring in the endpoint dedicated to the management of events having the corresponding XAMC event number.

When the tracking device detects this event, it generates an electrical signal Stop-X to the source, and more precisely to the control unit of the source, this having the effect of stopping the radiation. Provision may also be made for the tracking device to transmit at least one other electrical signal L, for example in order to turn on an indicator light managed by the control unit of the source. Specifically, it is conventional for x-ray sources to be equipped with a certain number of indicator lights (LEDs) for safety and informational purposes (for the practitioner or an assistant), in order to indicate whether the source is in the process of emitting or not, etc. It is therefore advantageous to be able to turn on (or turn off) a corresponding indicator light of the source when stoppage thereof has been commanded.

In practice, the signals output by the tracking device will for example be TTL logic signals transmitted via a coaxial cable connecting the tracking device and the source. The connector (BNC, DIN1.0/2.3, inter-alia) used to connect this cable to the source in practice depends on the connection interfaces available on the employed source.

Figure 7:
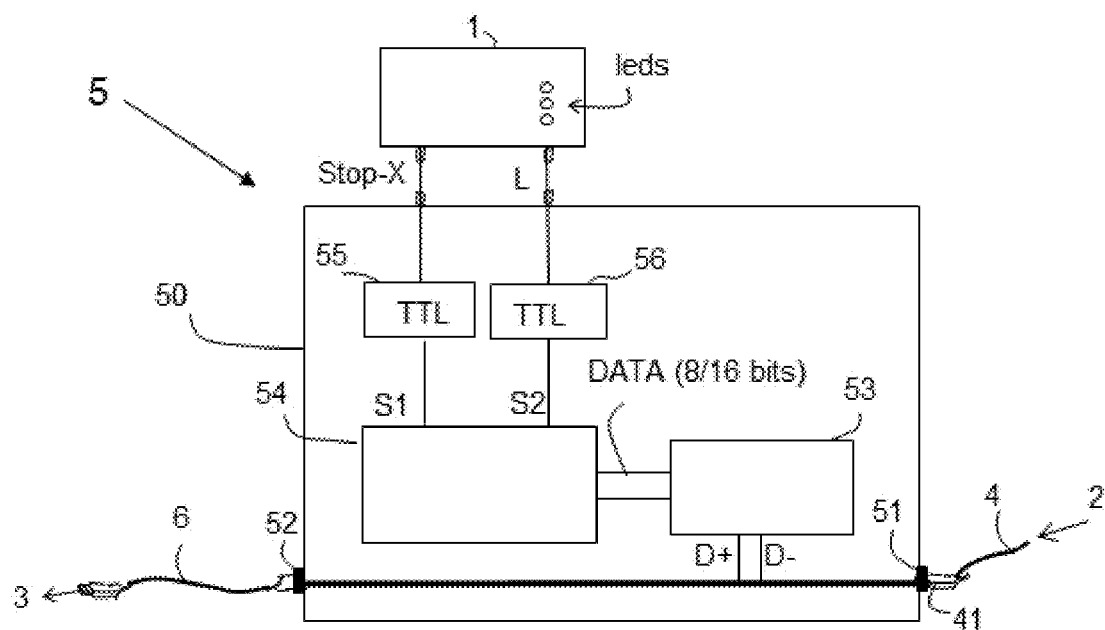
FIG. 7 is a block diagram of a tracking device according to the invention.

Such a tracking device 5 poses no practical implementational difficulties. Those skilled in the art may use commercial electronic circuits such as schematically shown in FIG. 7.

It is formed from a casing 50 that comprises a connector, for example a BNC connector, for connecting to the radiation source 1 and for transmitting the signal Stop-X and also the signal L where appropriate; a female USB connector 51 for receiving the male USB connector 41 of the USB interface 4 of the sensor; and a female USB connector 52 for the USB connection 6 to the computer 3. Between the 2 female connectors 51 and 52, extend the 4 conventional wires of the USB link: ground, logic voltage, and the two data wires D− and D+ (also called DM and DP in the technical literature).

Inside the casing, an electronic board comprises:
- a commercial circuit 53 that is a high-speed USB transceiver, which conventionally comprises a series interface port to which the two wires of the differential pair D− and D+ of the USB link are connected. It may thus read and decode the D− and D+ USB signal frames that are streamed over the USB link without interfering therewith, and it performs a series parallel conversion to deliver as output digital data over a (8- or 16-bit) parallel output bus DATA.
- a programmable logic circuit 54, for example a field-programmable gate array (FPGA), programmed to:
  detect in the data transmitted over the bus DATA by the circuit 53 frames of transfer interrupt type and, in these frames, the XAMC event, and
  activate, as output, one or more corresponding binary signals. In the example, the circuit 54 will activate to 1 a first signal S1 and a second signal S2 when it detects the XAMC event in the stream of data transmitted over the parallel bus DATA.
- a logic signal output stage, namely the circuits referenced 55 and 56 in the figure. Their role is to electrically adapt each of the logic signals S1 and S2 to the electrical interface with the source and to electrically isolate the programmable logic circuit 54. Typically, they are TTL signal output stages.

The casing 50 is supplied by an external power supply plugged into the mains.

The method and system for taking radiographical images that has just been described in the context of a particular dental application may be broadened to the more general medical context, provided that the image sensor used is connected by a USB link to a host device that receives and processes the image data of the sensor.

This method and system is based on the use of a data signal XAMC generated by the sensor and on detection of the transmission of a corresponding event over the USB link.

The signal XAMC is generated in the sensor by any technique known to those skilled in the art, by comparing the signal level of one or more pixels of the matrix to a threshold that is set, depending on the dynamic range and sensitivity of the sensor, to correspond to an optimal unsaturated signal level.

Preferably, it is generated by nondestructive read-out of these pixels. In this way, the information generated by these pixels may then be used in the image data. There is no loss of information as regards the image.

This principle of nondestructive read-out for the purposes of testing the signal level of the pixels is known to those skilled in the art. The reader may for example refer to the publications that were cited above, i.e. US2005/0253944 and U.S. Pat. No. 6,404,854B, for more details.

In practice, this nondestructive read-out is carried out by the control unit of the sensor, which performs the command-signal sequencing required to address the various pixels to be tested, connects them to the read-out and analogue-digital conversion circuits and ensures the transmission of the digital data obtained. Conventionally, the read-out and analogue-digital conversion circuits allow what is called a CDS read-out.

As explained above, in the integration phase, the control unit controls the circuits in order to read, over and over again, at least certain pixels, without reset after each read-out. For each read-out, the datum read is compared to a threshold; this comparison is for example made digitally in a FPGA programmable logic circuit conventionally provided, in the sensor, to process the digital data obtained from the pixels. The threshold is positioned for a given sensor to preferably correspond to ¾ of the dynamic range of the sensor. Provision may be made for the threshold to be programmed to a default value that may be parameterized by the practitioner via the computer and the USB link. When, for at least one pixel, and preferably for a plurality of pixels, the obtained signal level exceeds the threshold, the programmable logic circuit activates, as output, a corresponding binary data signal XAMC, for example by raising it to the level "1" if the convention adopted in the timing diagram in FIG. 5 is followed.

Figure 8:
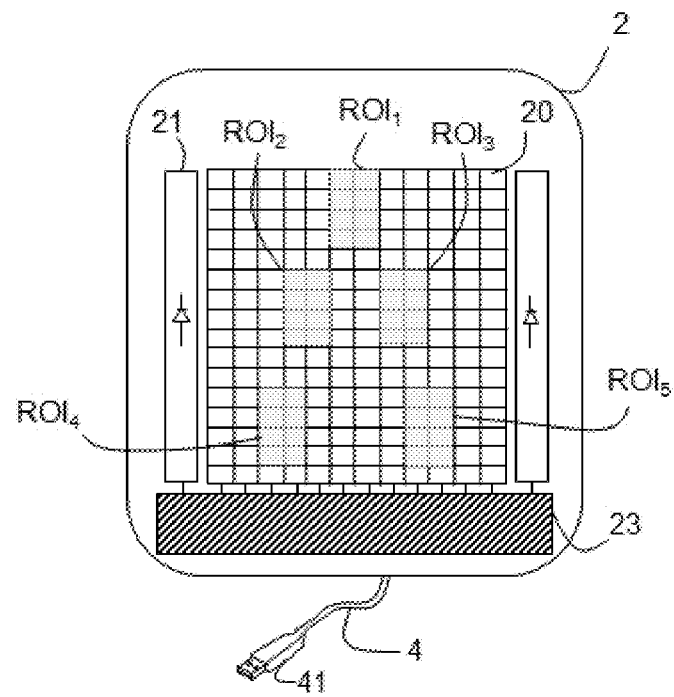
FIG. 8 is a schematic illustrating a sensor with regions of interest defined in the matrix of pixels to detect a sufficient duration of exposure to the x-ray radiation.
Figure 9:
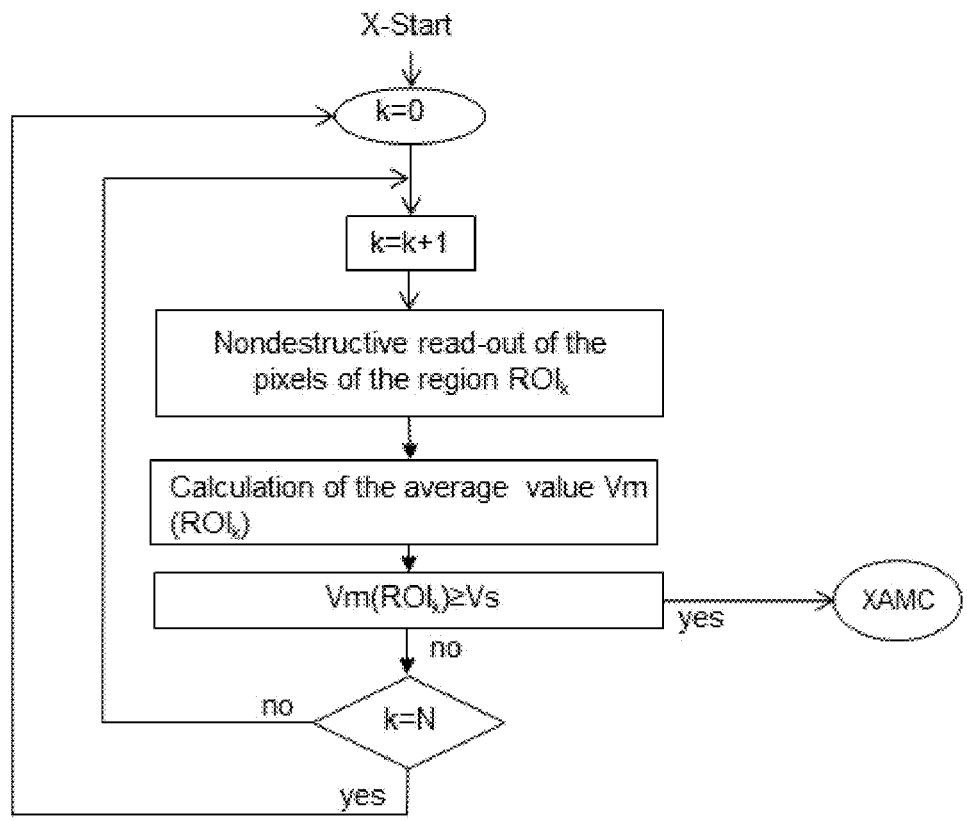
FIG. 9 is a flowchart showing an example of a loop for detecting a sufficient duration of exposure to the x-ray radiation by nondestructive read-out in the sensor of the one or more pixels of one or more regions of interest defined in a sensor such as illustrated in FIG. 8.

FIGS. 8 and 9 show a preferred exemplary embodiment of the detection, by the sensor, of the reception of a sufficient dose of radiation. What must be understood by "sufficient dose" is a dose at which the signal level reached by a number of pixels corresponds to an optimal unsaturated level, as explained above with reference to FIG. 4.

The detection must preferably be rapid and reactive since, as was seen above, the exposure very rapidly passes from the zone of optimal signal-to-noise ratio to a zone of signal saturation. The detection must also be reliable. The information contained in a single pixel is insufficient. A plurality thereof is required. However, it is not possible to read all the pixels of the matrix because this would take too long with regard to the average exposure times used.

Specifically, if for example an intra-oral sensor comprising 1.6 million pixels is considered, a complete read-out sequence at 5 MHz for example requires 381 ms, this being of the same order of magnitude as the times of exposure to a dose of x-rays used in radiology. If the sensor were larger, even more time would be required.

Rather than read in isolation a number of pixels of the matrix, in the invention it is advantageously proposed to:
define N regions of interest (N being at least equal to two) containing the same number of pixels and which are all of equal size both in number of rows and in number of columns, these regions thus forming sub-matrices of equal size.
calculate the average value of the signal level read from the pixels of one or more of the regions of interest thus defined; and it is the average value that is compared to a preset threshold value that depends on the characteristics of the sensor.

As the regions of interest are equal in number of pixels and also in number of corresponding matrix rows and columns, it is possible to compare the average values obtained to the same threshold; and the use of a plurality of regions of interest increases the probability that at least one of these regions will be at least partially well exposed to the radiation and not hidden (behind a tooth or another absorbing mass). Thus, a good detection reliability is obtained while enabling a low test loop time that is compatible with the desired detection. Preferably, in order to prevent the x-ray source from stopping too early, the average value obtained for a plurality of regions of interest may be compared to a threshold. Specifically, if a region of interest corresponds to a zone that is very weakly absorbent, it risks causing the x-ray source to stop too early, leading to an underexposure of other more interesting regions. This risk is decreased by taking the average of a plurality of regions of interest.

By way of illustration, FIG. 8 shows a sensor in which 5 regions $ROI_1$ to $ROI_5$ have been defined in the matrix of pixels according to these principles. In this example, each region is a sub-matrix of $2^3=8$ pixels arranged in two columns and four rows.

The advantage of providing a plurality of regions is that it increases the chance of testing a region that is at least partially not hidden from the radiation. The regions being strictly equal in shape and area, the average value calculated for these regions is comparable.

The number of pixels in the regions of interest and the number of regions of interest that it is possible to define must take into account the time required to read them: the greater the number of pixels to read in each region and the greater the number of regions, the greater the time required will be. In one example if 16 regions of interest are defined the size of which is 16 rows wide by 16 rows high, with a pixel read-out at 5 MHz it will typically be necessary to count 2.8 ms to read all the pixels.

Provision may advantageously be made for the definition (number of pixels, of rows and of columns), the number of regions of interest and their respective positions to advantageously be parameterizable, in particular depending on the object (tooth) of the patient, etc., from the computer via the USB link.

A loop for testing N regions of interest that may advantageously be implemented in a sensor according to this principle is illustrated by the flowchart in FIG. 9 in the case where it is desired to trigger an interruption of the x-ray source as soon as a threshold is exceeded by one region of interest; if it is desired to detect when the threshold is exceeded by the average of a plurality of regions of interest and not by the most exposed region of interest, this average will of course need to be calculated with a view to producing the signal XAMC. When the start of the radiation is detected by the sensor, the detection signal X-Start, which serves to activate the integration phase, will also allow the test loop to be activated. This activation may be immediate, or occur after a certain predefined time after the start of the integration phase, in order to ensure that the pixels will have begun to collect a minimum of charge.

The loop then initiates a counter of the number of regions to be tested and launches a pixel read-out loop, calculates the average value of the pixels and compares the average value to the preset threshold value, in each of the regions of interest.

As soon as the threshold value has been reached or exceeded by one region, the detection occurs: the test loop for the integration phase in course terminates with the corresponding detection signal XAMC being sent.

Provided that the result of the comparison is negative (threshold not reached or not exceeded), the loop passes to the following region of interest.

When the loop has tested the N regions and obtained a negative comparison result for each of the N regions, it resets the counter and the test restarts, until the threshold is detected to have been exceeded by at least one of the regions, or until the integration phase terminates after the preprogrammed period TINT. In the case where the test loop does not detect that the condition indicating that the threshold value has been reached or exceeded by at least one of the regions of interest, this may mean that the exposure time was not enough; this may mean that at least one of the parameters defining the regions of interest, namely their number, their size or their arrangement in the matrix, needs to be modified. Advantageously, provision will be made for these parameters to be programmable, via the device (3) and the USB link, allowing them to be adapted to the patient and to the object to be imaged.

The invention claimed is:

1. A method for taking images in a medical radiology system comprising an external x-ray source and a CMOS image sensor that is connected via a USB link by way of USB peripheral of a processing device for digitally processing the image data of the sensor, the method comprising using a tracking device for continuously reading and decoding the data transmitted over the USB link, in a way that is transparent to the processing device and to the sensor, in order to detect, in the transmitted data stream, one particular datum representing a signal indicating detection, by the sensor, that a sufficient dose of radiation has been received and, on detection of this particular datum, for sending an electrical signal to the radiation source in order to stop the emission of the radiation.

2. The method of claim 1, wherein on detection of this particular datum at least one other electrical signal is sent to the source, in order to command a display indicator light indicative of sufficient dose of radiation received.

3. The method of claim 2, comprising taking a dental radiological image with an intra-oral CMOS image sensor.

4. The method of claim 1, wherein said particular datum is a datum transmitted by the sensor over the USB link in an interrupt transfer mode.

5. The method of claim 4, comprising taking a dental radiological image with an intra-oral CMOS image sensor.

6. The method of claim 1, further comprising:
definition of N regions of interest in the matrix of pixels of the sensor, N being an integer at least equal to two, where the defined regions of interest are sub-matrices of pixels of equal size, all with the same number of rows and the same number of columns,
repeated and nondestructive read-out of the pixels of each of the regions of interest during the duration of the integration phase of the sensor, with, for each of the regions of interest, calculation of an average value of the signal level read from the pixels of the one or more regions of interest and comparison to a preset threshold value, and
a detection signal indicating that a sufficient dose of radiation has been received is activated by the sensor and a corresponding piece of information is transmitted over the USB link by the sensor as soon as, for one or more of the N regions of interest, the calculated average value exceeds the threshold value.

7. The method of claim 6, wherein the definition of the N regions of interest in the sensor is programmable, via the device and the USB link.

8. The method of claim 6, comprising taking a dental radiological image with an intra-oral CMOS image sensor.

9. The method of claim 7, comprising taking a dental radiological image with an intra-oral CMOS image sensor.

10. The method of claim 1 in which taking images is for taking dental radiological images and wherein the CMOS image sensor is an intra-oral CMOS image sensor.

11. A medical radiology system comprising an external x-ray source, a CMOS sensor comprising a matrix of pixels, which sensor is placed facing the source, and a device for digitally processing the images delivered by the sensor,
wherein the sensor is connected as a USB peripheral of said processing device, via a serial USB link:
the sensor is configured to detect that a sufficient dose of x-rays has been received and to transmit a corresponding particular datum over the USB link;
a tracking device connected to the USB link, between the sensor and the device, said tracking device furthermore having an electrical connection to the source, in order to transmit at least one electrical signal to the source in order to command the stoppage of the x-ray source, said tracking device being able to detect said particular datum in the data stream transmitted over the USB link, and to activate said electrical signal commanding the stoppage of the source.

12. The system of claim 11, wherein said electrical connection of the tracking device with the source transmits at least one other signal to the source in order to command a display indicator light.

13. The system of claim 12, wherein said tracking device comprises at least:
one USB transceiver that is connected to the data wires of the USB link, in order to transmit as output the data transiting the USB link over a parallel bus,
a programmable logic circuit that is programmed to detect said particular datum among said data received from the parallel bus and to activate as output at least one logic signal that is transmitted to the source to command the stoppage of the radiation.

14. The medical radiology system of claim 13 and applied in the field of dental radiology, wherein the sensor is an intra-oral CMOS image sensor.

15. The medical radiology system of claim 12 and applied in the field of dental radiology, wherein the sensor is an intra-oral CMOS image sensor.

16. The system of claim 11, wherein said tracking device comprises at least:
one USB transceiver that is connected to the data wires of the USB link, in order to transmit as output the data transiting the USB link over a parallel bus, a programmable logic circuit that is programmed to detect said particular datum among said data received from the parallel bus and to activate as output at least one logic signal that is transmitted to the source to command the stoppage of the radiation.

17. The medical radiology system of claim 16 and applied in the field of dental radiology, wherein the sensor is an intra-oral CMOS image sensor.

18. The medical radiology system of claim 11 and applied in the field of dental radiology, wherein the sensor is an intra-oral CMOS image sensor.

* * * * *